US007056279B2

(12) United States Patent
Verberckmoes et al.

(10) Patent No.: US 7,056,279 B2
(45) Date of Patent: Jun. 6, 2006

(54) DEVICE AND METHOD FOR ARTIFICIAL INSEMINATION OF BOVINES AND OTHER ANIMALS

(75) Inventors: Steven Verberckmoes, Grembergen (BE); Ann Van Soom, Zomergem (BE); Aart De Kruif, Afsnee (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 10/363,827

(22) PCT Filed: Sep. 4, 2001

(86) PCT No.: PCT/EP01/10181

§ 371 (c)(1),
(2), (4) Date: May 18, 2004

(87) PCT Pub. No.: WO02/19943

PCT Pub. Date: Mar. 14, 2002

(65) Prior Publication Data

US 2004/0199044 A1 Oct. 7, 2004

(30) Foreign Application Priority Data

Sep. 5, 2000 (EP) .................................. 00870190

(51) Int. Cl.
*A61B 17/43* (2006.01)

(52) U.S. Cl. ......................... 600/35; 604/515; 604/906

(58) Field of Classification Search ............ 600/33–35; 604/514–517, 906

See application file for complete search history.

(56) References Cited

U.S. PATENT DOCUMENTS 3,877,430 A 4/1975 Wieder
4,493,700 A 1/1985 Cassou et al.
5,496,272 A 3/1996 Chung et al.
5,916,144 A 6/1999 Li et al.
6,071,231 A 6/2000 Mendoza et al.

FOREIGN PATENT DOCUMENTS

EP 0 071 538 2/1985
EP 0 538 786 4/1993
FR 2 647 668 12/1990

OTHER PUBLICATIONS

Acta Vet. Scand. 1998, 39, 149-163 "Deep Uterine Insemination of Cattle: A Fruitful Way Forward with Smaller Numbers of Spermatozoa", Hunter and Greve.

Theriogenology (May 1998, vol. 29, No. 5, p. 1131-1142), Hawk et al., "Fertilization Rates in Superovulating Cows After Deposition of Semen of the Infundibulam, Near the Uterotubakl Junction or After Insemination With High Numbers of Sperm" Hawk et al.

*Primary Examiner*—John P. Lacyk
(74) *Attorney, Agent, or Firm*—Knobbe, Martens, Olson & Bear, LLP

(57) ABSTRACT

An artificial insemination (AI) device for the insemination of bovines and other animals including three hollow and essentially cylindrical tubular elements. Each element is provided with an open proximal and an open distal end, the three elements being: an outer protective sheath, an inner sheath, and a semen tube, whereby the diameter of the elements is such that the inner sheath is axially movable in the outer protective sheath and the semen tube is axially movable in the inner sheath, whereby the length of the outer sheath is less than the length of the inner sheath and whereby the inner sheath and the semen tube are jointly axially displaceable in and through the outer sheath. An outer sheath, an inner sheath and a semen tube for use in an AI device and a method for the insemination of bovines and other animals, includes the steps of inserting through the cervix and into the uterine horn, a closed tubular element to a point near the major curve of the horn, opening the tubular element by protrusion of an inner tubular element and manually guiding it into the curve of the horn and positioning the distal end of the inner tubular element near the ovary, and further providing semen nearby the UTJ through an internal semen channel.

27 Claims, 2 Drawing Sheets

DEVICE AND METHOD FOR ARTIFICIAL INSEMINATION OF BOVINES AND OTHER ANIMALS

RELATED APPLICATIONS

This application is a national phase entry in the United States of the International Application PCT/EP01/10181 filed Sep. 4, 2001, and claims the benefit of Application 00870190.6 filed Sep. 5, 2000, in the European Patent Office.

FIELD OF THE INVENTION

The present invention relates to a method and a device for the artificial insemination of bovines and other animals.

DESCRIPTION OF RELATED ART

Worldwide, artificial insemination (AI) has penetrated about 80% of the dairy industry but only about 5% of the beef producing industry. One reason is the need for skilled personnel, veterinarians and technicians, trained to grasp the cervix via the rectum and to guide the AI pipette into or through the cervix.

In the traditional AI, the inseminator must insert the insemination tube into the cervix by developing the tactile skill to work through the wall of the large intestine while pushing the tube forward through the vagina with the other hand. The cervix is more than 10 cm long (10,16–15,24 cm in beef cattle) and often has several bends (e.g. "s" or "v" shape in some Brahman cattle), and has several very tight sphincters through which the AI tube must be guided. Hence there is the ever present danger of perforating the wall of the cervix or the uterus with the inseminating tube, causing injury to the animal. Because of these difficulties, it is often impossible to advance the inseminating tube very far into the cervix, with a corresponding lower insemination efficiency and conception success rate.

Several artificial insemination devices are known, for example as disclosed in U.S. Pat. No. 6,071,231 and U.S. Pat. No. 4,493,700.

An overview article on AI is found in Acta Vet. Scand. 1998, 39, 149–163 "Deep Uterine Insemination of Cattle: A fruitful Way Forward with Smaller Numbers of Spermatozoa" by Hunter and Greve. As in the present invention the importance of the site of fertilization and of spermatozoa deposition, i.e. near the utero-tubal junction (UTJ) is explained.

While these devices and methods have been a great advancement in artificial insemination, reducing time, expenses and effort, and increasing effectiveness, there are still a number of problems.

The major disadvantage of the deposition of the semen at the posterior end of the uterus is the great loss (about 60%) of the inseminated semen. Only about 40% of the insemination remains in the female genital tract and only 0.1% of this reaches the place of fertilization in the oviduct.

One problem is that these devices do not deliver the optimum quantity and concentration of semen that will maximize the probability of conception since there is no way to assure that all of the semen is transferred from its storage straw into the uterus of the animal without any losses.

Another problem is that these devices do not simplify the deliverance of the optimum insemination dose and diluting fluid required to accommodate the cervices and uteri of animals of varying sizes since there is no way to vary the dose while preserving the optimum quantity and concentration of semen.

Due to the extreme curvature of the uterine horn when a cow is in oestrus, deposition of semen is normally performed in the cranial part of the cervix or in the uterine body. Seldom, the semen is deposited in the major curve of the uterine body. The distance of the ejected semen towards the mature ovum in the oviduct remains considerable and results in a lower insemination efficiency and conception success rate. In contrast to pigs, in cows normally only one oocyte per cycle ovulates unless they are hormonally treated for superovulation. Because cattle is a monovular species, it is very important that the semen is present in the top of the uterine horn at the site of ovulation. Because palpation of the ovaries often causes rupture of the mature follicle and loss of the occyte in the abdomen, the side of the ovulation is usually not determined during insemination. This means that a lot of sperm is needed to establish fertilization in one of both oviducts, at the side of ovulation if the semen is deposited at the cranial end of the uterus.

The article "Fertilization rates in superovulating cows after deposition of semen on the infundibulum, near the uterotubal junction or after insemination with high numbers of sperm" in Theriogenology (May 1998, Vol. 29, No. 5, p1131–1142), Hawk et al. describes a method and device comprising three pieces of non-standard equipment for insemination at the uterotubal junction consisting of:

a) a stainless steel tube 60 cm long, 6.3 mm outside diameter and 4.4 mm inside diameter for penetrating the cervix;

b) a flexible teflon tube (TFS No. 9[d]) 90 cm long and 4 mm outside diameter for passing through the uterine horns; and c) a nylon rod 105 cm long to expel semen from the teflon tube. A round epoxy bead was formed around one end of the teflon tube to facilitate passing the tube through the uterine horns. Two cotton plugs with polyvinyl-chloride powder between them were inserted into the end of the teflon tube adjacent to the epoxy bead and there was a 1 ml air space between the plugs and the end of the tube. The nylon rod was marked to permit expulsion of semen in 0.5 ml quantities. Although this device is an improvement on site of deposition of the semen in the uterine horn, this device requires the use of cotton plugs and nylon rods which need to be manipulated by at least two skilled people.

According to the method disclosed by Hawk in the above-mentioned publication, semen is housed in a tube closed off with cotton plugs on one end. A syringe fitted with a length of tygon tubing was used to transfer 1 ml of the semen into the teflon insemination tube. The teflon tube is then inserted into the stainless steel sheat, so that the epoxy bead was seated into one end of the steel tube. The use of such a tube is only possible in a recti-linear manner. It is impossible to move the cotton plugs and the polyvinyl chloride forward through the teflon tube if it makes a sharp curvature of the contractile uterus of a cow.

In these known methods semen is lost at various steps of the operation. Some semen is left behind in the storage tube when it is mixed with the diluting fluid in the ampule. Some semen is also left behind in the ampule when the semen mixed with diluting fluid is aspirated into the pipette. And finally, some semen is left behind in the pipette when the semen mixed with diluting fluid and loaded in the pipette is pushed with air or a nylon rod out of the pipette.

These losses of semen produce an inseminating fluid charge with a low sperm concentration and a corresponding low fertilization success rate. In addition, the insemination dose and diluting fluid cannot be readily adjusted to accommodate the various sizes of cervix and uterus found among animals of different sizes, breeds and species. Thus an insemination device with an improved ability of delivering an optimum quantity and concentration of semen, and that lends itself to delivering an optimum insemination dose and diluting fluid, is desirable.

OBJECTS OF THE INVENTION

Accordingly it is an object of the invention to provide an artificial insemination (AI) device and method for bovines and other animals with improved semen delivery.

It is also an object of the invention to provide an AI device and method, which deliver the optimum quantity and concentration of semen.

It is another object to deliver the optimum of quantity of semen near or as close as possible near the utero-tubal junction (UTJ), where fertilization takes place.

It is another object of the invention to provide an AI device and method, which delivers an optimum insemination dose and diluting fluid.

It is a further object of the invention to provide an AI device and method, which will optimize the fertilization success rate regardless of the decreased sperm quality and the varying sizes of the animals.

It is another object to provide an AI device and method providing an improved delivery site for the semen near the utero-tubal junction.

Another important object of the invention is to deposit the semen as close to the fertilization place as possible, avoiding contamination of the uterine environment.

It is another object to inseminate as close as possible to the place of fertilization without causing damage to the uterine mucosa, and certainly without perforating the uterine wall.

It is another object of the invention to provide a method and device that can be adapted to other animals and for other compounds, such as antibiotics and embryo's.

A final important object of the invention is to develop an insemination instrument and technique, which prevents spreading of venereal diseases (Bovine Viral Diarrhoea, Bovine Herpesvirus-1, Campylobacter Foetus) from one cow to the other in or between different livestocks.

SUMMARY OF THE INVENTION

The AI device according to the invention comprises an artificial insemination device for the insemination of bovine and other animals comprising three hollow and essentially cylindrical tubular elements, each element is provided with an open proximal and an open distal end, said three elements being:

an outer protective sheath, an inner sheath, and a semen tube, whereby the diameter of said elements is such that the inner sheath is axial movably in the outer protective sheath and the semen tube is axial movably in the inner sheath and whereby the length of the outer sheath is less than the length of the inner sheath and whereby the inner sheath and the semen tube are jointly axially displaceable in and through the outer sheath. The AI device according to the invention is especially adapted for the introduction of semen, but may also be used for the delivery of antibiotics or other pharmaceuticals and even for embryo's.

The use of inner and outer sheath makes it possible to provide an improved positioning of the distal end of the AI device according to the invention. The use of three elements results in a suitable site of deposition for the semen, i.e. near the utero-tubal junction. This suitable deposition site is obtained via two main steps. First step is performed mainly by the introduction of the rigid outer sheath, which encloses at least the distal part of the inner sheath and the semen tube. The distal end of the outer sheath is positioned through the cervix of the vagina and extends close to the uterine wall. A subsequent positioning step is obtained via the protrusion of at least a flexible part i.e. the distal end of the inner sheath jointly with the semen tube through the outer sheath. Due to the flexible material of the distal end of the inner sheath and the semen tube a curve is made such that the distally extendillg end reaches easily a position near the UTJ. This second positioning step is preferably controlled by manual guidance of the distal end of the protruded flexible part of the inner sheath and the semen tube. Once in a suitable position near the utero-tubal junction semen is ejected. The semen introduction near the UTJ is performed with less spoilage due to the fact that the semen tube is a separate element housed in the inner sheath. The semen is during the expelling operation protected by the enveloping or covering action of the inner sheath, which is especially adapted therefor. The inner sheath is provided with a flexible distal part and suitable closure means for partially closing off the semen tube. As a consequence less spoilage of semen occurs during the overall positioning of the combination semen tube and inner sheath. The introduction of the semen is an intentional and controlled action once the distal end of the inner sheath with the expelling opening for the semen has reached a suitable position near the utero-tubal junction. The semen is expelled with a specific action such as an air pressure pulse performed on the proximal end of the semen tube. The semen is forced out of the semen tube only when it is in a suitable deposition site. The distal end of the semen tube is enclosed in the inner sheath. Preferably the distal end of the semen tube is in a frictional contact with the inner wall of the inner sheath. When the inner sheath protrudes through the outer sheath, the semen tube will—passively—follow the movement of the inner sheath.

In a preferred embodiment an artificial insemination is provided wherein the inner sheath comprises at least a rigid part and a flexible part. The use of said flexible part provides an advantage, i.e. has the possibility of following the curvature of the uterine horn without damaging the uterine wall. In the preferred embodiment the distal end (introduced in the cervix and uterus) of the flexible part is provided with a cervix protector element having at least one ejection port which preferably extends at least partially in the radial direction of the inner sheath. Such a specific ejection port is suitable for ejection of semen when required and closes off the outer sheath and the semen tube during their positioning. Provided with said cervix protector element the joint introduction of the outer sheath and the semen tube can be performed with lowered risk of harm to the cervix of the bovine to be inseminated.

More preferred embodiments of the present invention are disclosed in sub-claims 5–15 and will be elucidated with reference to the drawings.

The invention is also related to a method for the insemination of bovines and other animals. In general the method according to the invention comprises two position steps for positioning the distal end of an AI device. In the first step the position of rigid tubular element, the outer sheath is performed through the cervix into the uterus. In the first introduction step the semen tube and the inner sheath are partly enveloped by the outer sheath. The proximal end of the semen tube and the inner sheath extends through the proximal opening of the outer sheath. Preferably the semen tube is essentially completely introduced in the inner sheath. The closure means of the inner sheath simultaneously closes off the outer sheath and the semen tube. In a second positioning step the flexible part of the inner sheath together with the semen tube is further introduced via protrusion through the outer sheath into the uterine horn near the UTJ. The closure means of the inner sheath closes off the semen tube during this introduction. Once the distal part of these joint tubes has arrived near the UTJ a controllable delivery of the semen is performed. The semen is forced out of the semen tube through a radial opening in the closure means of the inner sheath. In the present invention the inseminated bovine is exposed to lowered risk of harm and more of the available sperm is delivered on a suitable position. If necessary, manual guidance of the distal end of the inner sheath can assist the positioning of the distal end. When the suitable position of the distal end is obtained semen can be ejected. All these manipulations can be performed by one person, such as the inseminator only.

BRIEF DESCRIPTION OF THE DRAWINGS

Further features and advantages of the invention will be apparent from the ensuing description which is given merely by way of example with reference to accompanying drawings in which.

DETAILED DESCRIPTION OF THE INVENTION

Figure 1:
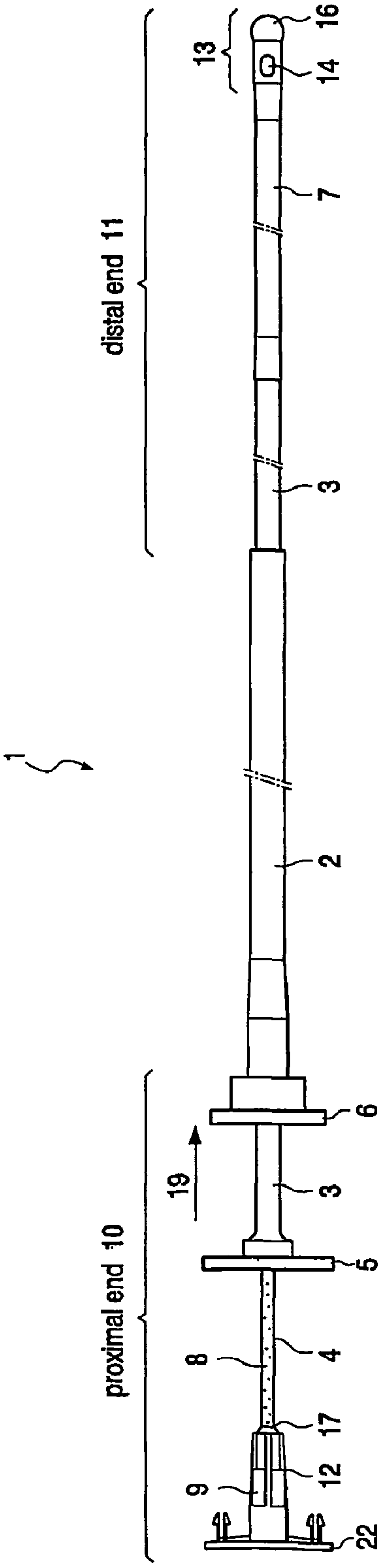
FIG. 1 shows an overview of an artificial insemination assembly according to the invention, the three parts are interrupted in the longitudinal direction, it being understood that, at the scale at which it is represented, the complete length would be distinctly greater than the length of the drawing sheet.

The entire artificial insemination assembly 1 comprises three hollow cylindrical open or semi-open tubular elements, which are each axially movable in a sliding motion mounted in one another as shown in FIG. 1. These three elements are: an outer protective and rigid sheath 2 suitable for the penetration of the cervix, an inner sheath 3 and the semen tube 4. The diameter of those three elements is such that the semen tube 4, having the smallest diameter, is axially movable in the inner sheath 3, and the inner sheath 3 is axially movable in the outer sheath 2. The outer sheath 2 has a length which is smaller than the length of the inner sheath 3 and is made out a rigid material suitable for penetrating the cervix.

The proximal end 10 of the AI device 1 is the end which protrudes out of the bovine during insemination allowing at all times a manipulation of the outer and the inner sheath and of the semen tube at which ends an external manual handling is performed. The distal end 11 of the AI device 1 is the end which takes position in the reproductive organ of the bovine when insemination is performed.

The outer sheath has a rigid cylindrical form and is closed off via the cervix protector element 16 provided on the inner sheath. The cervix protector element 16 is attached at the distal end of the inner sheath 3. In a suitable position of the inner sheath 3, i.e. extending partly on the proximal side, the cervix protector element 16 closes the outer sheath 2. A closed outer sheath 2 carrying partly the inner sheath 3 and the semen tube 4 is introduced through the anterior vagina, the cervix in a rectilinear movement, up to a position when the distal end of the inner sheath makes contact with the uterine wall. Once this straight lined introduction of the outer sheath enveloping partly the inner sheath and the semen tube a curve extension will be necessary in order to reach a suitable position near the UTJ.

The inner sheath 3 is axial movable mounted in the outer sheath 2 and has at its proximal end, a small annular handling disc or thumb rest 5 which permits shifting the inner sheath by means of the thumb of the user into a position touching the finger flange 6 of the outer protective sheath 2. This sliding action results in a protrusion of a flexible part 7 of the inner sheath 3 into the uterine horn. Manipulation by hand will guide said flexible part 7 around the major curve of the uterine horn and will position the distal end near the UTJ. Semen content 8 in the semen tube can at this position be delivered nearby the UTJ. The inner sheath 3 has a tubular body which is adapted to receive at one end a supply of semen contained in an open semen tube 4.

Figures 2A, 2B:
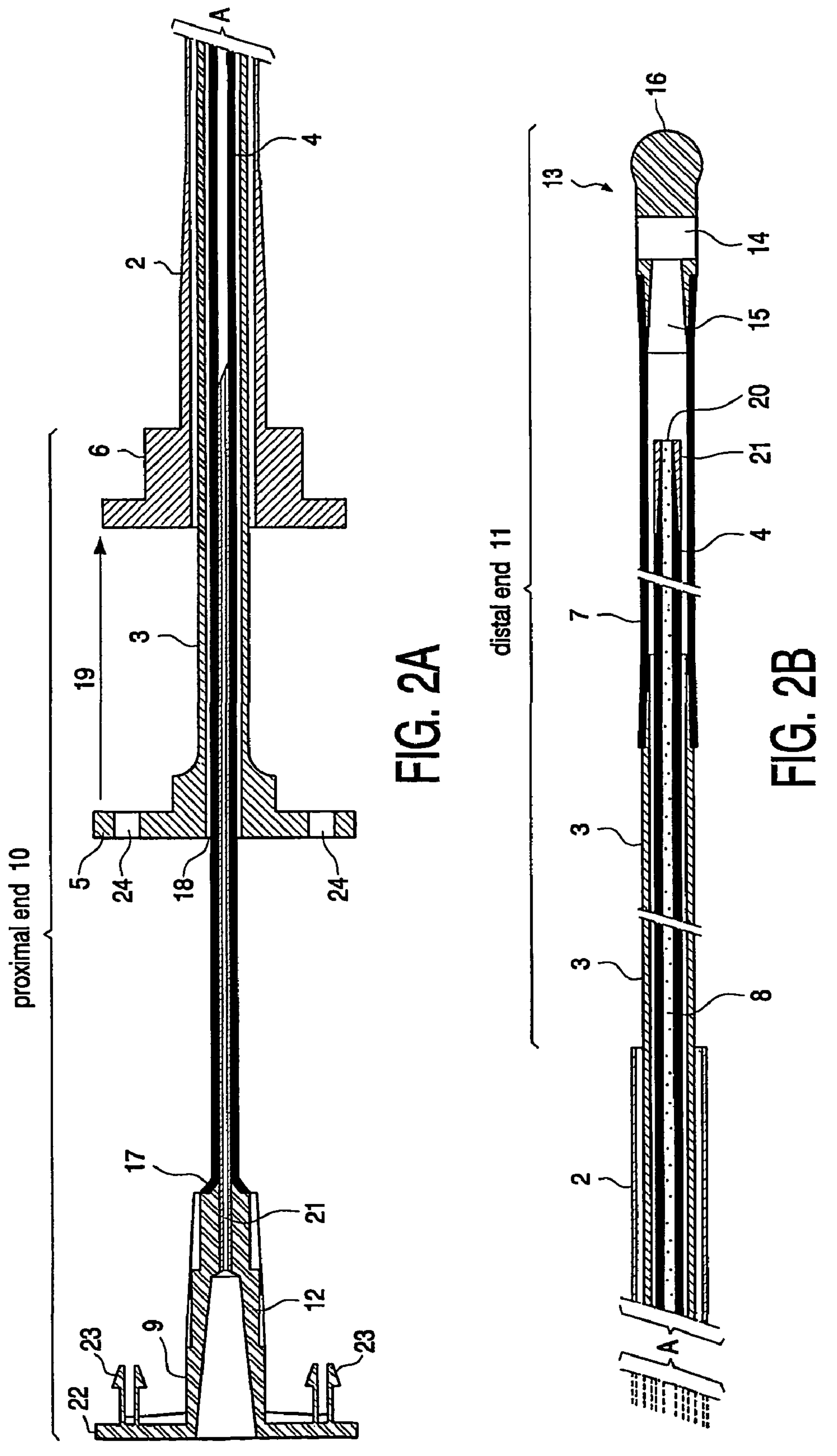
FIGS. 2*a* and 2*b* show cross sectional views of the proximal and distal end respectively of an artificial insemination assembly according to the invention.

The inner sheath 3 is provided with cervix protector means 13 for protecting the cervix of the bovine. Said cervix protector means 13 will close off completely the outer sheath 2 and will close off at least partly the semen tube thereby limiting entrance of uterine contents. Due to the specific form of the cervix protector means, less spoilage of any semen (closing off the semen tube) is assured during the introduction of the AI device. Furthermore, the rounded tip avoids damage to the uterine wall when introduced. Once the outer sheath is introduced a joint introduction of the flexible part of the inner sheath and the semen tube will be performed. The cervix protector has a smooth end 16. During the complete introduction of the AI device this smooth end will protect the uterine lumen. The tube containing the semen is free of toxic components that could be harmful to cells. The top of the inner sheath is preferably a round enlarged top, from which the inner diameter decreases to the top 15 (FIG. 2B). This reduces loss of semen between the insemination tube and the inner sheath.

The path of the flexible part of the inner sheath and the semen tube in the uterine lumen can be followed through the wall of the large intestine by rectal palpation. The exact positioning of the semen deposition can be located by palpating the cervix protector element of the inner sheath.

For hygienic reasons the AI device according to the invention is preferably made of disposable materials, for single use only. As an example hereunder dimensions and materials are listed for each element in table 1.

The flanges on the proximal end 10 of the inner sheath 3 limit the inner sheath 3 accidentally coming out of the outer sheath 2. The semen tube 4, which is inserted in the inner sheath 3, is fixed to it by frictional means caused by the insertion of an injection needle 21, (FIG. 2A) in the tube 4. This needle 21 also provides a good fixation of the syringe on the tube 4 and into the inner sheath 3. The cervix protector element of the inner sheath 3 closes the inner and outer sheath, to limit dirt entering the instrument when it is inserted into the female genital tract. This reduces contamination of the uterine environment and semen.

The semen tube 4 is made out of a flexible material and is provided with adaptor means 9 at its proximal end 10. These adaptor means 9 comprise in the depicted embodiment a needle hub (LuerLock®-coupling 12) for housing a syringe. This syringe will force the semen 8 in and out the semen tube 4.

The semen tube 4 is axial movably mounted in the inner sheath 3. The adaptor means 9 could be a syringe or a plunger-rod adapted to expel the semen from the tube and prior to the insemination to suck up the semen from a semen container. The semen tube has a total volume within a range of 0.25–1 ml and preferably from about 0.5 ml.

Semen of a chosen bull (Cassou straw of 0.25 ml) is normally preserved in a closed container with liquid nitrogen. In the classic insemination technique, the straw is thawed and opened at one side and inserted in the insemination instrument. The semen is expelled by moving the cotton plugs forward by means of a stainless steel rod. For the insemination instrument according to the invention, straws can be used. The straws are first thawed at 37° C. during one minute and then the semen (0.25 ml) is then expelled in an ampule which contains 0.25 ml sodium citrate. The total of 0.5 ml is sufficient for a successful insemination by the deposition of 0.25 ml semen solution for each uterine horn.

The use of an open semen tube at the distal end is an advantage for the filling of the semen tube with the semen originating from a semen container. The use of a suction device, for example a syringe at the proximal end of the semen tube will force the semen out of the container into the semen tube. Less semen is wasted in this way in the filling of the semen tube. As the semen tube is separate element used in the AI device according to the invention and herein only serving for the transport deposition of semen in a site, less semen is lost in the deposition, i.e. insemination step. Ejection of semen out of the semen tube through the distal end of the inner sheath (the cervix protection means 13) is also done under control of a pushing or forcing device, which can be a syringe. As it becomes apparent a syringe is a preferred tool for filling and emptying the semen tube. Semen can also be "sexed" i.e. detected on the X and Y sex chromosome, for example by the use of known techniques, such as flow cytometry or immunological techniques.

The inner 3 and outer 4 sheath is of the type having a thickness which is substantially constant throughout its length and having at a first open end, the proximal end or insemination end distal end.

Due to the slightly broadened frusto-conical element 17 at the overlap of the adaptor means 9 at the proximal end 10 of and the semen tube 4 it is possible to lock the semen tube 4 on the inner sheath 3. This rubbing contact, which is also a result of the widening of the diameter of the tube 4 by the insertion of the needle 21, between the element 17 and the annular opening 18 of the flange 5 will result in a combined axial movement of the tube 4 with the inner sheath 3. When pushing the thumb rest or finger flange 5 toward the finger flange 6 of the outer sheath 2 the semen tube will migrate along over the same distance or will retard a little.

Once the flexible part 7 of the inner sheath 3 protrudes through the outer sheath 2, the distal end of the semen tube will be forced to make the same sliding movement. The flexible part 7 of the inner sheath 3 can be manually guided into the uterine horn. When the distal end of the inner sheath 3 is close to the UTJ a suitable semen deposition site is obtained. With the same hand, which has performed the axial movement of the flanges (5,6) guide, an expelling instrument, such as preferable a syringe, the semen 8 is expelled out of the semen tube 4 through the ejection port 14 near the UTJ. This is an important advantage of the present invention. One person only, i.e. the inseminator, can perform the insemination, using one arm and hand to guide the flexible part 7 of the inner sheath and the other for the control of the axial movement at the proximal end of the elements 2,3 and 4, and the control of the expelling instrument for expelling the semen out of the semen tube.

In order to improve the smooth movement of the semen towards the deposit side near the UTJ the semen tube is locked onto the inner sheath. For these purposes a frictional fixation is available or separate fixation means can or may be provided on the proximal end of the semen tube 9 by means of fixation legs 23 which are provided on a separate flange 22. A corresponding protrusion 24 is provided on the flange 5 of the inner sheath 3. The semen tube 4 and the inner sheath 3 are when joined together axially moveable in and through the outer sheath 2. In order to further improve a smooth movement and more in particular a smooth curved movement of the joint parts, i.e. the flexible part of the inner sheath 3 and the semen 4, a tubular rigid tip is proved at the distal end of the semen tube. Preferably, this is a small cylindrical metal tip made of stainless steel which will lower the risk of tendency for bending or cracking. Semen is deposited immediately in the ejection part.

The insemination device according to the invention limits damage to the sperm, caused by environmental factors (light, cold). It is not transparent and made of materials with a low heat conductivity. Light causes an increase of oxidation reactions and release of reactive oxygen species, which causes membrane damage of the spermatozoa and death. A sudden decrease beneath 15° C. causes a cold shock effect in the spermatozoa and death.

The insemination technique according to the invention makes it possible to use:

a. lower number of spermatozoa in the inseminate b. frozen-thawed sperm cells that are especially vulnerable to passage along the full extent of the uterus c. sexed sperm cells (separated X and Y chromosone bearing spermatozoa) available in relatively low numbers d. sperm cells whose DNA status may have been modified by specific treatment.

It should be clear that the present invention is not restricted to bovine nor to insemination of semen. Other animals, for example horses, deer, etc. can be treated in a similar way. Embryos, antibiotics and other compounds and compositions can also be delivered using the present device and method.

As a practical example preferred lengths and preferred materials of the components of the AI device are given in table I.

TABLE 1

| Element | Length | Internal diameter | External diameter | Material |
|---|---|---|---|---|
| Outer sheath 2 | 50 cm | 3.2 mm | 5.5 mm | PS-SB |
| Inner sheath 3 | 55 cm | 1.95 mm | 3.0 mm | ABS |
| Outer flange 6 | 3.0 mm | 3.10 mm | 1.7 cm | PVC |
| Inner flange 5 | 3.0 mm | 4.7 mm | 1.7 cm | PVC |
| Cervix protection means | | | 5.0 mm | ABS |

TABLE 1-continued

| Element | Length | Internal diameter | External diameter | Material |
|---|---|---|---|---|
| Flexible part 7 | 16 cm | 2.5 mm | 3.0 mm | PVC |
| Semen tube 4 | 73 cm | 1.0 mm | 1.8 mm | PE |
| Semen tube metal end | 2.5 cm | 1.0 mm | 1.8 mm | STAINLESS STEEL |

The invention claimed is:

1. An artificial insemination device for the insemination of bovines and other animals comprising three hollow and cylindrical tubular elements, wherein each element is provided with an open proximal and an open distal end, said three elements comprising:

an outer protective sheath;

an inner sheath, and;

a semen tube, whereby the diameter and arrangement of said elements is such that the inner sheath is axially movable in the outer protective sheath and the semen tube is axially movable in the inner sheath, whereby the length of the outer sheath is less than the length of the inner sheath and of the semen tube and wherein the inner sheath and semen tube are substantially equal in length, and wherein, the inner sheath and the semen tube are jointly axially displaceable in and through the outer sheath.

2. An artificial insemination device according to claim 1, wherein the inner sheath comprises at least a rigid part and a flexible part.

3. An artificial insemination device according to claim 2, wherein the inner sheath comprises a rigid part near the proximal end and a flexible part near the distal end, wherein both parts are axially interconnected forming a passage for the semen tube.

4. An artificial insemination device according to claim 3, wherein the flexible part at the distal end is provided with a cervix protector element having an ejection port for the ejection of semen and configured for closing off the outer sheath.

5. An artificial insemination device according to claim 3, wherein the flexible part has a length from 1 cm to 40 cm.

6. An artificial insemination device of claim 3, wherein the inner sheath is provided at its proximal end with a handling disc.

7. An artificial insemination device of claim 1, whereby the outer sheath is provided at a proximal end with a finger flange.

8. An artificial insemination device of claim 1, whereby the length of the outer sheath is from 40–60 cm.

9. An artificial insemination device of claim 1, whereby the two sheaths are made of disposable material.

10. An artificial insemination device of claim 1, wherein the semen tube is flexible.

11. An artificial insemination device of claim 1, whereby the semen tube is provided with an adaptor for coupling of a semen expelling instrument.

12. An artificial insemination device according to claim 11, whereby the adaptor is formed by a needle hub for a syringe as a semen expelling instrument.

13. An artificial insemination device of claim 1, wherein a distal end of the semen tube is provided with a tubular rigid semen tube end.

14. An artificial insemination device of claim 1, whereby a proximal end of the semen tube is provided with a fixation for coupling the semen tube into the inner sheath.

15. The artificial insemination device of claim 1, wherein the outer sheath comprises a cylindrical tubular body with an open distal end and open proximal end, and a finger flange at the proximal end having a length of 40–60 cm and made out of rigid disposable material.

16. The artificial insemination device of claim 1, wherein the inner sheath comprises a cylindrical tubular hollow body with an open proximal end and a at least partly open distal end provided with a finger flange at the proximal end having a first rigid part having a length of 20–60 cm and a second flexible part having a 5–30 cm and made out of a disposable material.

17. The artificial insemination device of claim 1, wherein the semen tube comprises a cylindrical tubular hollow body made out of a flexible and disposable material with an open distal end and at a proximal end is provided with an adaptor for a syringe.

18. The artificial insemination device of claim 5, wherein the flexible part has a length from 5–30 cm.

19. The artificial insemination device according to claim 18, wherein the flexible part has a length from 10–20 cm.

20. The artificial insemination device of claim 8, wherein the length of the outer sheath is from 45–55 cm.

21. The artificial insemination device of claim 9, wherein the disposable material comprises a synthetic plastic.

22. An artificial insemination device for the insemination of bovines and other animals comprising three hollow and cylindrical tubular elements, wherein each element is provided with an open proximal and an open distal end, said three elements comprising:

an outer protective sheath;

an inner sheath, and;

a semen tube wherein a distal end of the semen tube is provided with a tubular rigid semen tube end, whereby the diameter and arrangement of said elements is such that the inner sheath is axially movable in the outer protective sheath and the semen tube is axially movable in the inner sheath, whereby the length of the outer sheath is less than the length of the inner sheath, and wherein, the inner sheath and the semen tube are jointly axially displaceable in and through the outer sheath.

23. An artificial insemination device for the insemination of bovines and other animals comprising three hollow and cylindrical tubular elements, wherein each element is provided with an open proximal and an open distal end, said three elements comprising:

an outer protective sheath;

an inner sheath, whereby a proximal end of the semen tube is provided with a fixation for coupling the semen tube into the inner sheath and;

a semen tube, whereby the diameter and arrangement of said elements is such that the inner sheath is axially movable in the outer protective sheath and the semen tube is axially movable in the inner sheath, whereby the length of the outer sheath is less than the length of the inner sheath, and wherein, the inner sheath and the semen tube are jointly axially displaceable in and through the outer sheath.

24. Method for insemination of bovines and other animals, comprising the steps of inserting through the cervix and into the uterine horn, a closed tubular element assembly of three nested tubular elements comprising an innermost semen tube axially movable within an intermediate inner sheath and with the inner sheath axially movable within an outermost protective sheath and wherein the semen tube and inner sheath have substantially the same length to a point near the major curve of the horn, opening said tubular element assembly by extending the semen tube and the inner sheath and manually guiding the semen tube and the inner sheath into the curve of the horn and positioning a distal end of the semen tube and the inner sheath near the ovary, and providing semen nearby the utero-tubular junction (UTJ) through the semen tube.

25. Method according to claim 24, wherein the semen is provided once a distal end of the semen tube has been positioned near the utero-tubal junction.

26. Method for insemination of a bovine whereby an inseminator uses one hand to guide a distal end of a nested inner sheath and semen tube which are both at least partially flexible while his second hand is used to manipulate axial movement of a proximal end of the inner sheath and semen tube to extend the distal end of the inner sheath and semen tube into the curved portion beyond the cervix.

27. Method for insemination of a bovine according to claim 26, whereby his second hand is used to control a semen expelling device.

* * * * *

UNITED STATES PATENT AND TRADEMARK OFFICE

CERTIFICATE OF CORRECTION

PATENT NO. : 7,056,279 B2

APPLICATION NO. : 10/363827

DATED : June 6, 2006

INVENTOR(S) : Verberckmoes et al.

It is certified that error appears in the above-identified patent and that said Letters Patent is hereby corrected as shown below:

TITLE PAGE

Section (75), Inventors, line 2 delete "($_m$BE)" and insert --(BE)--.

Section (73), Assignee, delete "Ghent" and insert --Gent--

Section (56), line 7 of Other Publications, delete "Uterotubakl" and insert --Uterotubal--

COLUMN 2

Line 17 delete "occyte" and insert --oocyte--

COLUMN 4

Line 19 delete "extendillg" and insert --extending--

COLUMN 8

Line 44 delete "chromosone" and insert --chromosome--

Signed and Sealed this

Twelfth Day of December, 2006

JON W. DUDAS

*Director of the United States Patent and Trademark Office*